United States Patent [19]
Winter et al.

[11] Patent Number: 5,932,617
[45] Date of Patent: *Aug. 3, 1999

[54] WOUND-TREATING COMPOSITION AND METHOD

[75] Inventors: Rudolph E. K. Winter; Adewole L. Okunade; Memory P. F. Elvin-Lewis; Walter H. Lewis, all of St. Louis; Ali Kasiri, Columbia, all of Mo.

[73] Assignee: WoundFast Pharmaceuticals Inc., St. Louis, Mo.

[ * ] Notice: This patent is subject to a terminal disclaimer.

[21] Appl. No.: 09/021,225

[22] Filed: Feb. 6, 1998

[51] Int. Cl.[6] ............ A61K 31/165; A61K 31/19; A61K 31/195; A61K 31/235
[52] U.S. Cl. ............ 514/533; 514/539; 514/563; 514/568; 514/616; 424/447
[58] Field of Search .................. 514/533, 539, 514/563, 616, 568; 424/447

[56] References Cited

U.S. PATENT DOCUMENTS 3,694,557  9/1972  Persinos .................. 424/279

(List continued on next page.)

OTHER PUBLICATIONS

Russell Ross, "The Fibroblast and Wound Repair", May 15, 1967, Biol. Rev. 43 (1968), pp. 51–96, Plates 1–15.

(List continued on next page.)

*Primary Examiner*—Phyllis Spivack
*Attorney, Agent, or Firm*—Rothwell, Figg, Ernst & Kurz, P.C.

[57] ABSTRACT

A cell-proliferation promoting and wound-healing composition and method utilizing a compound or salt of Formula (I),

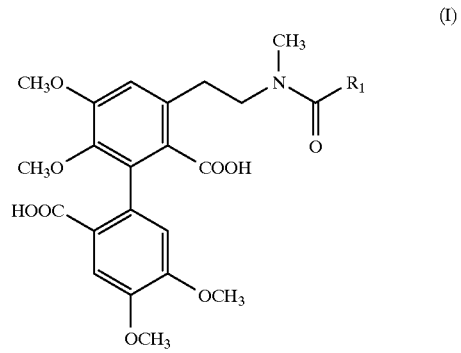

(I)

in which $R_1$ is $(CH_2)_n CH_3$ wherein n is 0 to about 10; Formula (II),

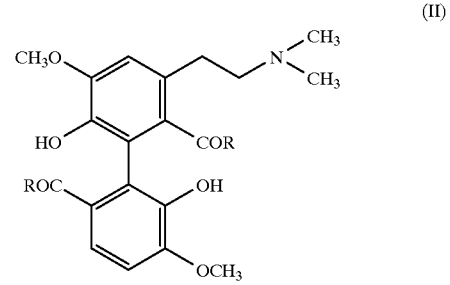

(II)

in which R is $NH(CH_2)_a CH_3$ or $O(CH_2)_a CH_3$, wherein a is 0 to about 10; Formula (III)

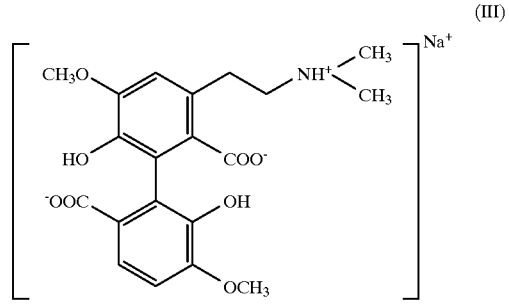

(III)

23 Claims, 3 Drawing Sheets

U.S. PATENT DOCUMENTS

| | | | |
|---|---|---|---|
| 4,120,964 | 10/1978 | Hartenstein et al. | 424/258 |
| 4,183,939 | 1/1980 | Gieske et al. | 424/258 |
| 4,597,961 | 7/1986 | Etscorn | 424/28 |
| 4,782,077 | 11/1988 | de la Parra | 514/423 |
| 4,844,901 | 7/1989 | Keplinger et al. | 424/195.1 |
| 5,069,904 | 12/1991 | Masterson | 424/401 |
| 5,156,847 | 10/1992 | Lewis et al. | 424/447 |
| 5,474,782 | 12/1995 | Winter et al. | 424/443 |

OTHER PUBLICATIONS

Erle E. Peacock, "Collagenolysis and the Biochemistry of Wound Healing", Wound Repair, (1984), pp. 102–140.

Southern and Buckinham, *Dictionary of Alkaloids,* Chapman and Hall, London and New York, summary from pp. xxiv–xxv (1989).

Beatriz H. Porras–Reyes et al., "Enhancement of Wound Healing by the Alkaloid Taspine Defining Mechanism of Action (43567)", Taspine Improves Wound Healing, May 19, 1992, vol. 203, pp. 18–25.

Georgia Persions Perdue et al., "South American Plants II: Taspine Isolation and Anti–Inflammatory Activity", Journal of Pharmaceutical Sciences, vol. 68, No. 1, Jan. 1979, pp. 124–126.

W. H. Lewis, "Introduction To The Ethnobotanical Pharmacopeia Of The Amazonian Jivard Of Peru", Medicinal and Poisonous Plants of the Tropics, Pudoc Wageningen, The Netherlands, 1987, pp. 96–103.

Robert Thornton Morrison et al., "Solubility", Organic Chemistry, Third Edition, Dec. 1973, Table of Contents, pp. 30–33.

Abraham J. Vaisberg et al., "Taspine is the Cicatrizant Principal in Sangre de Grado Extracted from *Cronton lechleri**"*, Planta Medica 55, (1989), pp. 140–143.

Merriam–Webster, Inc., "Webster's Third New International Dictionary . . . Unabridged", (1986), pp. 108, 1707, 2405.

Thomas A. Mustoe et al., "Accelerated Healing of Incisional Wounds in Rats Induced by Transforming Growth Factor–β", Reports, Science vol. 237, (1987), pp. 1333–1336.

T.P. Plantanova et al., "Study of Plant Alkaloids", *Leontice ewersmannli,* BGE, IV. Structure of the Alkaloid Taspine (1), (1956) pp. 2957–2961.

WOUND-TREATING COMPOSITION AND METHOD

BACKGROUND OF THE INVENTION

1. Field of the Invention

The present invention relates to compositions and methods used for healing of wounds and proliferating cells in culture.

2. Description of the Background Art

There is continuing medical interest in materials and methods which promote and accelerate the healing of wounds. Wound-healing strength can be measured in newtons (N) or expressed in $g/mm^2(\times 1000/9.8)$ (Tensometer 10, Monsanto Co., St. Louis, Mo., U.S.A.) utilizing a linear skin incision model in rats, as is well documented (Ross, "The Fibroblast and wound repair", *Biological Review* 43: 51–96 (1968); Peacock, Jr., "Wound Repair", Ed. 3, W. B. Saunders, Philadelphia (1984); Mustoe et al., "Accelerated healing of incisional wounds in rats induced by transforming growth factor-β", *Science* 237: 1333–1335 (1987)). This is a recognized model in assessing a generation of wound strength, the most important aspect of wound-healing (Mustoe et al., supra).

As described in U.S. Pat. No. 5,156,847, issued Oct. 20, 1991 to Lewis et al., U.S. Pat. No. 5,474,782, issued Dec. 12, 1995 to Winter et al., and in Porras-Reyes et al., *Proc. Soc. Exp. Bio. Med.* 203: 18–25 (1993), wound-healing compositions of the alkaloid taspine, dissolved in a non-aqueous solvent, such as dimethyl sulfoxide (DMSO) were shown to promote wound healing. However, taspine is practically insoluble in most conventional vehicles, including water, alcohol, saline solutions, and the like. Thus, there remains in the art a need for new compositions and methods which can be effectively, safely, and economically administered and utilized to accelerate the healing rate of wounds, and which preferably are soluble in aqueous media.

Additionally, Lewis et al., Winter et al., and Porras-Reyes et al. show promotion of wound-healing solely by measuring tensile strength using a linear skin incision rat method. Accordingly, there is a need in the art for new methods in addition to the linear skin incision model in rats which allow direct observations and measurements of wound-healing acceleration in taspine and taspinates and their aporphine-derived analogs and other aporphine-derived compounds. Also, there is a need in the art to provide new methods showing fibroblast and other types of cellular proliferation necessary to accelerate wound repair and appropriate modeling.

SUMMARY OF THE INVENTION

In accordance with the present invention, a wound-treating composition comprises a compound of the Formula (I),

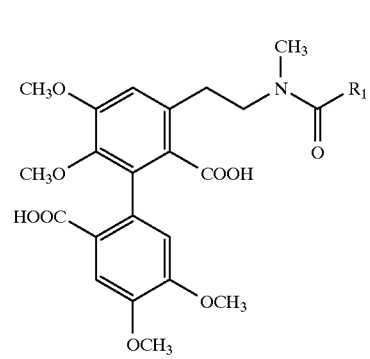

in which $R_1$ is $(CH_2)_nCH_3$ wherein n is 0 to about 10, Formula (II),

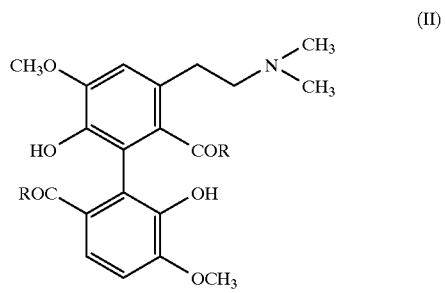

in which R is $NH(CH_2)_aCH_3$ or $O(CH_2)_aCH_3$ wherein a is 0 to about 10, and Formula (III),

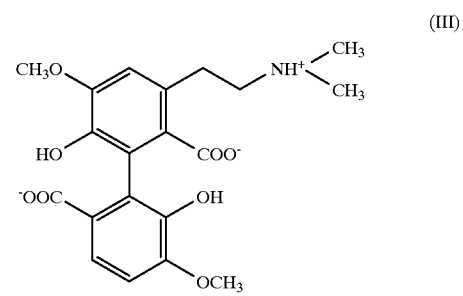

Also disclosed are wound dressings and methods of treating wounds utilizing a compound or a mixture of compounds selected from the group consisting of Formula (I), Formula (II), Formula (III) or pharmaceutically acceptable salts thereof. Also disclosed are methods for direct observations of wound healing through reepithelialization and closure of wounds in swine and rabbit using Formula (III) in a new formulation to increase solubility.

DETAILED DESCRIPTION OF THE INVENTION

Figure 1:
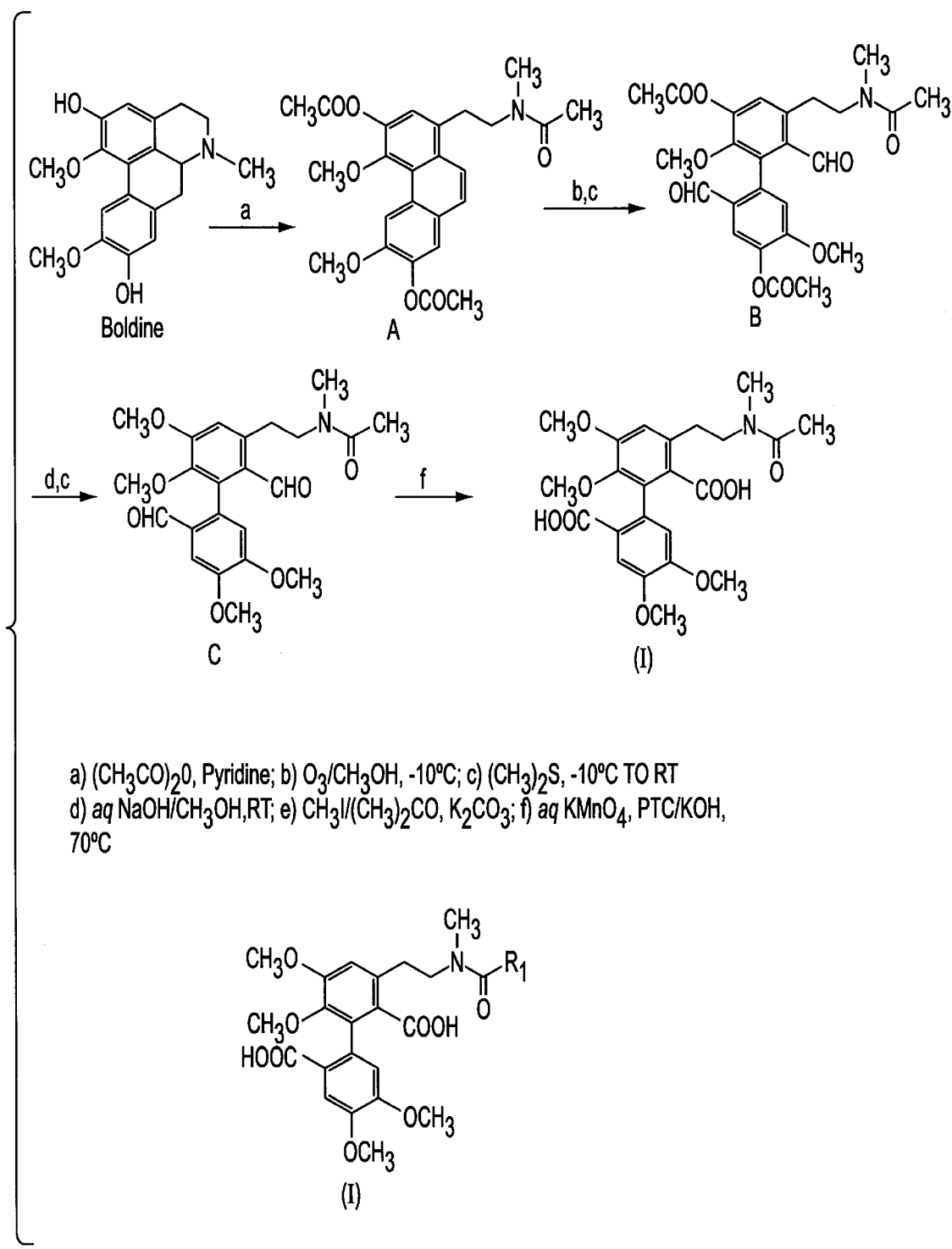
FIG. 1 is an overall scheme for the synthesis of the compound of Formula (I), wherein $R_1=CH_3$.

According to one aspect, the present invention is applicable to a compound selected from the group consisting of Formula (I), Formula (II) and Formula (III), supra, including all tautomeric forms thereof, and including the pharmaceutically acceptable salts thereof, and mixtures thereof.

The term "pharmaceutically acceptable salts" may include salt-forming cations selected from the group consisting of cations of alkali metals, alkaline earth metals, copper, zinc, manganese, nickel, ammonia and organic ammonium. The term "alkali metals" includes lithium, sodium, potassium, cesium, and rubidium; and the term "alkaline earth metals" includes beryllium, magnesium, calcium, strontium and barium.

In a preferred embodiment of Formula (I), n is 0 to about 5, even more preferably, n is 0.

Additionally, in a preferred embodiment of Formula (II) a is 0 to about 5, more preferably, a is 0.

The term "pharmaceutically acceptable amides" may include those carboxyl amides of Formula (II) prepared from low molecular weight organic amines, i.e., having a molecular weight less than about 400, and such organic amines including alkyl amines and alkanol amines which in preferred embodiments, include two or fewer amine groups, such as methyl amine, dimethyl amine, ethyl amine, diethyl amine, N-propyl amine, isopropyl amine, butyl amine and benzyl amine; primary aryl amines, such as aniline, o,m,p-methoxy and ethoxy aniline, o,m,p-toluidine, and phenylenediamine. Specific examples include alkyl (methyl, ethyl, n-propyl, n-butyl) carboxyl amides.

Additional "pharmaceutically acceptable amides" include N-amides analogous to Formula (I) obtained from aporphine alkaloids, such as boldine, isocorydine, apomorphine, corytuberine, isoboldine, apocodeine, and similar aporphines, and which in preferred embodiments are those prepared with low molecular weight acid anhydrides and acid chlorides, such as those derived from simple aliphatic acids, aryl carboxylic acids, and derivatives of simple amino acids, which in preferred embodiments include acetic acid, propionic acid, butyric acid, benzoic acid, glycine, phenylalanine, and the like. Specific examples include N-methylamide of Formula (I) and analogous N-methylamides of isocorydine and apomorphine.

Formula (II) may include carboxyl esters prepared from low molecular weight alcohols, i.e., having a molecular weight less than about 300, and such organic alcohols including alkyl alcohols, which in preferred embodiments include two or fewer alcohol groups, such as methanol, ethanol, n-propanol, isopropanol, butanol, cyclopentanol, menthol, benzyl alcohol, and o,m,p-methoxybenzyl alcohols. Specific examples include alkyl (ethyl, isopropyl, N-butyl) carboxyl esters.

In preferred embodiments, physiologically acceptable or tolerable liquid carriers of Formulae (I) and (II) are standard saline (0.9% saline solution), buffered saline, a deionized, aqueous solution of 10% isopropanol, pH 7.5–7.8 (NVF), or their mixtures, administered substantially topically, subcutaneously, or the like. The level of significance of wound healing in swine using, for example, NVF at 300 μg/wound area of the compound of Formula (I) was P<0.004. Furthermore, no significant effects have been found, either irritating and hence, negative, or healing and thus positive, on the saline and NVF solution alone when compared to controls.

In a particularly preferred embodiment of the present invention, a physiologically acceptable or tolerable liquid carrier of Formula (III) is a deionized, aqueous solution of about 1–25% by volume isopropanol, preferably about 5–15% by volume isopropanol, and most preferably 10% isopropanol (NVF). The levels of significance of wound healing in swine and rabbit using NVF solutions of the compound of Formula (III) were P<0.001 to P<0.0005, respectively. Furthermore, no significant effects have been found, either irritating and hence negative, or healing and thus positive, of the NVF solution alone when compared to controls.

A particularly preferred physiologically acceptable or tolerable liquid carrier of tissue culture in the present invention is minimum essential medium (MEM) with compounds of Formulae (I), (II) and (III), following stock solution preparation in Hanks balanced salt solution (HBSS) for Formulae (I) and (II) and 10% isopropanol solutions for the Formulae (III). The levels of significance of fibroblast proliferation of the compounds of Formulae (I), (II) and (III) peaked at $P<0.3\times10^{-5}$ (375 μg/mL), $P<0.2\times10^{-6}$ (750 μg/mL), and $P<0.7\times10^{-5}$ (750 μg/mL), respectively.

The compounds of the present invention can be applied to a wound in a pharmaceutically acceptable liquid carrier, such as standard saline or NVF, wherein the compound is at a concentration of from about 150 μg/mL to about 500 μg/mL, expressed in terms of taspine-equivalents. Compositions in accordance with the present invention can include the inventive compounds and their biologically active analogs in a liquid carrier at wound healing concentrations expressed in terms of equivalents of taspine, described in U.S. Pat. No. 5,156,847 and U.S. Pat. No. 5,474,782, incorporated herein by reference. In such wound healing concentrations, the inventive compounds and their analogs thereof include about 0.05–5 mg/mL, or preferably about 0.1–1 mg/mL, and most preferably about 0.15–0.5 mg/mL, or concentrations referenced to standard solutions. Alternatively, the inventive compounds and their analogs can be present in a form such as a cream, salve, foam, lotion, collagen preparation, gel, ointment and alcohol.

Figure 3:
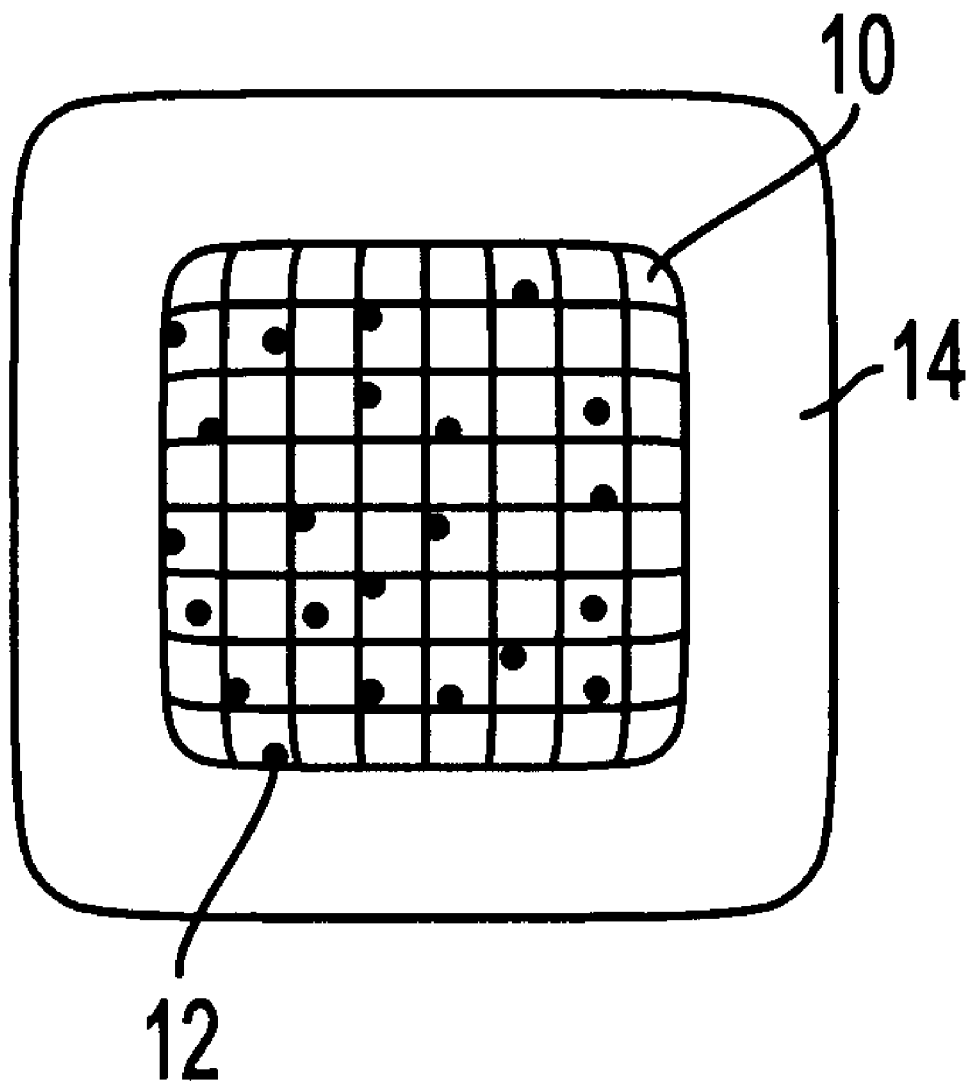
FIG. 3 is an elevational view, partially schematic, of a prepackaged wound dressing with a sterile bandage including the wound-healing compound or a mixture of compounds in accordance with one embodiment of the present invention.

The present invention is also applicable to a wound dressing, and preparations thereof. In accordance with this aspect of the invention, a wound dressing includes a sterile bandage, gauze, or collagen preparation 10, onto which the inventive compound, or its salt, amide, or ester 12 is deposited or applied and may be dried or moistened as further described in U.S. Pat. No. 5,474,782, incorporated herein by reference, and is provided in sterile packaging 14 (see FIG. 3).

In one method of treating wounds in accordance with the present invention, a wound healing effective amount of a compound or composition in accordance with the present invention, or a pharmaceutically acceptable salt, amide, or ester, is applied to the wound. In preferred embodiments, the inventive compounds, salts, amides, or esters are applied to the wound so as to provide the wound with about 0.05–5 mg/cm², more preferably about 0.1–0.5 mg/cm², and most preferably about 0.15–0.4 mg/cm², of the inventive compound, expressed in terms of taspine-equivalents.

Advantageously, the inventive compounds, salts, amides or esters are applied to a wound site after cleansing thereof if necessary, either as a single application, or as a plurality of administrations over a period of time during healing. In preferred embodiments, the inventive compounds, salts, amides, or esters are applied at least once a day for one or several days or for up to seven or more days after wounding or initiation of treatment.

The present invention is also applicable to inducing cellular proliferation by addition of an inventive compound, or a composition containing an amide, ester, or salt of a compound selected from the group of Formula (I), Formula (II), Formula (III), or a mixture thereof. Cells capable of proliferation by addition of compounds and preparations of the present invention include those from cell lines of animal origin, e.g., human, including those which are of transgenic or recombinant nature, as recipients of genomic material (nucleic acid sequences naturally or artificially conceived and defined as articles of manufacture, and derived either in vitro or in vivo). Cell lines capable of proliferation by addition of the compounds and compositions of the present invention include cell lines of ectodermal, endodermal, and mesodermal origin, including those of primary and continuous (serially propagated diploid, heteroploid, polyploid, or aneuploid) origin.

In a preferred embodiment of the present invention, the cells in which cellular proliferation occurs according to the invention are fibroblast cells. Fibroblast proliferation can take place in from 1 minute to about 72 hours, more preferably from 1 minute to about 48 hours, and most preferably from 1 minute to about 24 hours.

Modalities for stimulating cellular proliferation may include the use of specific solvents, vehicles, or culture media for delivery of the compounds of the present invention and during the initial treatment phase of the tissue culture. Depending on the cell line, proliferation may be supported and also enhanced by the use of specific synthetic, serum-free media or basic growth media requiring serum, hormones, growth factors, cytokines, or other organic or inorganic molecules needed for optimal cell propagation and acceleration. Temperatures for treatment and proliferation may vary, depending on cell sources.

The invention is illustrated by the following examples, which are not intended to be limiting:

EXAMPLE I

Preparation of Wound-Healing Semisynthetic Taspinic Amides

The isolation of the natural alkaloid taspine from which the semisynthetic compounds are derived is detailed in U.S. Pat. No. 5,474,782, incorporated herein by reference.

A. Taspinic N-amides of Formula (I)

The preparation of N-amido analogs of taspinic acid is illustrated by synthesis of Formula (I), wherein $R_1=CH_3$, starting with boldine. The overall scheme is shown in FIG. 1.

Conversions of boldine to a phenanthrene derivative was accomplished by heating the hydrochloride in acetic anhydride containing 5% pyridine at 115° C. Dilution with 1% aqueous cupric sulfate, extraction with chloroform and chromatographic purification furnished A. Ozonolysis of A was carried out in methanol at -10° C. so that only one equivalent of ozone was absorbed. Subsequent treatment with dimethyl sulfide and warming to room temperature resulted in a single peroxide-free product, dialdehyde B, which was isolated by extraction and purified by flash chromatography. In order to avoid potential complications resulting from acetate hydrolysis concomitant with oxidation, B was first converted to the O,O,O',O'-tetramethyldialdehyde C. Thus, treatment of B with basic methanol at room temperature was followed by oxygen methylation in refluxing acetone using methyl iodide and potassium carbonate. Finally, dialdehyde C was treated with an aqueous potassium permanganate solution (2%) containing tricaprylylmethyl ammonium chloride as phase transfer catalyst (PTC) and potassium hydroxide added; the mixture was stirred vigorously while heating to 70° C. Acidification gave the N-acetamidodicarboxylic acid Formula (I), wherein $R_1=CH_3$.

Formula (I) and its analogs may also include N-alkyl secondary amines and N,N-dialkyl tertiary amines obtained from Formula (I) and its analogs with in preferred embodiments methyl and/or ethyl alkyl groups.

B. Taspinic acid carboxyl amides of Formula (II)

The preparation of carboxyl amides is illustrated by the synthesis of Formula (II), wherein $R=-NHCH_3$.

A mixture of purified taspine and excess aqueous solution of methylamine (40%) was refluxed for 2 hours. The resulting clear solution was concentrated in vacuo. The residue was dissolved in deionized water, filtered, frozen, and lyophilized to provide the compound of Formula (II), wherein $R=-NHCH_3$.

EXAMPLE II

Wound Reepithelialization and Closure in Swine using Taspinic N-amide of Formula (I) and Monosodium Salt of Formula (III)

Solutions of N-amide of the Formula (I) and the monosodium salt of the Formula (III) both in NVF at concentrations of 300 µg/wound area taspine-equivalents were tested on swine back wounds against NVF alone (Table 1). Wounds were made using a biopsy punch 6.3 mm in diameter and 2–5 mm deep, and after experimental and control solutions were administered at day 0, the wounds were covered with Tegaderm®. After harvesting at day 4 or 5, histological sections were examined for epithelial regrowth and wound closure. Tests and histological analyses were conducted under blind conditions. Results and their statistical analyses using the paired T test (2-tailed) were based on 2 adult swine (I) and 3 juvenile swine (III).

Reepithelialization and closure of wounds 4 or 5 days after administration of concentrations of 300 µg/wound area taspine-equivalents of the experimental N-amide and monosodium salt solutions in NVF compared to NVF alone (control) are shown in Table 1. Results showed highly significant levels of wound-healing by both experimental taspinic N-amide ($P<0.004$) and monosodium taspinate ($P<0.001$).

These differences (in mm) were confirmed by percent increases of wound closure using both the experimental taspinic N-amide and monosodium salt in NVF compared to NVF control. At 300 µg/wound area after 4 or 5 days wound closure accelerated from 32% to 54% in Formula (I) and from 46% to 68% in Formula (III), increases of 68% and 49% over controls, respectively.

TABLE 1

| Compound + C1 | RE (mm) (M ± SEM) | Closure (%) | C1-RE (mm) (M ± SEM) | C1-Closure (%) | P |
|---|---|---|---|---|---|
| Formula (I) | 3.39 ± 0.29 | 53.86 | 2.02 ± 0.42 | 32.05 | <0.004 |
| Formula (III) | 4.07 ± 0.26 | 67.94 | 2.74 ± 0.23 | 45.71 | <0.001 |

(I): Wound (X = 5) reepithelialization (RE) and closure (%) using the adult swine back model, biopsy punch wounds 6.3 mm diameter and 4–5 mm deep after 5 days, 1 application 300 μg in NVF day 0, C1 (NVF control).
(III): Wound (X = 15) reepithelialization (RE) and closure (%) using the juvenile swine back model, biopsy punch wounds 6.3 mm diameter and 2–3 mm deep after 4–5 days, 1 application 300 μg in NVF day 0, C1 (NVF control).

EXAMPLE III

Wound Reepithelialization and Closure in Rabbits using the Monosodium Taspinate of Formula (III) in NVF Solutions of monosodium taspinate of the Formula (III) in NVF at a concentration of 150 μg/wound area taspine-equivalents were tested on rabbit ear wounds against NVF (C1) and no treatment control (C3). Wounds were made using a biopsy punch 6.3 mm in diameter and 1.5 mm deep, and after experimental and NVF solutions were administered at day 0, the wounds together with the no treatment wound control were covered with Tegaderm®. After harvesting at day 7, histological sections were examined for epithelial regrowth and wound closure. Tests and histological analyses were conducted under blind conditions.

Reepithelialization and closure of wounds 7 days after administration of a concentration of 150 μg/wound area taspine-equivalents of the experimental Formula (III) in NVF compared to NVF alone (C1) and no treatment (C3) are shown in Table 2. Results illustrated a significant difference of $P<0.05$ between Formula (III)+C1 and C1, and a highly significant difference of $P<0.0005$ between wounds treated with Formula (III)+C1 and those with no treatment (C3).

These differences measured in mm were confirmed by percent increases of wound closure between Formula(III)+C1 and two controls, C1 alone and no treatment (C3). At 150 μg/wound area after 7 days, wound closure accelerated from 56.30% to 86.94% when Formula (III) was compared to C1 control and from 38.36% to 86.94% when Formula (III) was compared to C3 control, increases in wound closure of 54% and 127%, respectively.

TABLE 2

| Component + C1 (NVF) | RE (mm) (M ± SEM) | Closure (%) | (M ± SEM) | % | P |
|---|---|---|---|---|---|
| | | | C1-RE (mm) | C1-Closure | |
| Formula (III) | 5.48 ± 0.36 | 86.94 | 3.55 ± 0.62 | 56.30 | <0.05 |
| | | | C3-RE (mm) | C3-Closure | |
| | | | 2.42 ± 0.40 | 38.36 | <0.0005 |

(III): Wound (X = 8) reepithelialization (RE) and closure (%) using the rabbit ear ulcer model, biopsy punch to cartilage 6.3 mm diameter and 1.5 mm deep after 7 days, 1 application 150 μg in NVF/wound area day 0, C1 (NVF control) (X = 8) and C3 (no treatment control) (X = 6).

EXAMPLE IV

Tissue Culture of Fibroblasts in Taspinic N-amide of Formula (I) wherein $R_1$=$CH_3$, Taspinic carboxyl amide of Formula (II) wherein R=—NHCH$_3$, and Monosodium Taspinate of Formula (III) at Various Concentrations The fibroblasts of GM00468A, a primary, aging normal skin line, were grown in tissue culture for 24 hours in concentrations of 50–750 μg/mL of Formulae (I), (II) and (III).

Stock solutions of taspinic amides of Formulae (I) and (II) were made in buffered Hank's Balanced Salt Solution (HBSS) and the monosodium taspinate of Formula (III) was solubilized in NVF at concentrations of 2 mg/mL. For testing, the protocol followed that of Promega's CellTiter 96®, Aqueous Non-Radioactive Cell Proliferation Assay, a calorimetric method to determine by tetrazolium salt staining the number of viable cells in proliferation. The compounds were diluted in tissue culture medium (Minimum Essential Medium with Earle's salts and L-glutamine (MEM), and consisting of 1% vitamins, 2% nonessential amino acids, 2% essential amino acids, 20% fetal bovine serum) to reach final concentrations ranging from 0 (no compound) to 1.5 mg/mL, and dispensed in 200 μL/well aliquots into 96-well tissue culture plates containing $10^5$ GM00468A cells seeded 24 hours previously and incubated at 37° C. Peplicate wells (4–10) were tested per compound concentration. After incubation for 24 hours, 20 μL of a mixture containing tetrazolium salt dye prepared by mixing 2 mL of a 2 mg/mL solution of the dye (Promega G1111) with 100 μL of a 0.92 mg/mL solution of phenzine methosulfate (Sigma P9625) was added to each well followed by 4 hours of further incubation before reading in a BIO-TEK microplate autoreader (EL311SX). The adjusted optical density (OD) is recorded as degrees of light absorbance, minus the media blank, with the higher the absorbance reflected as an increase in living cells.

Figure 2:
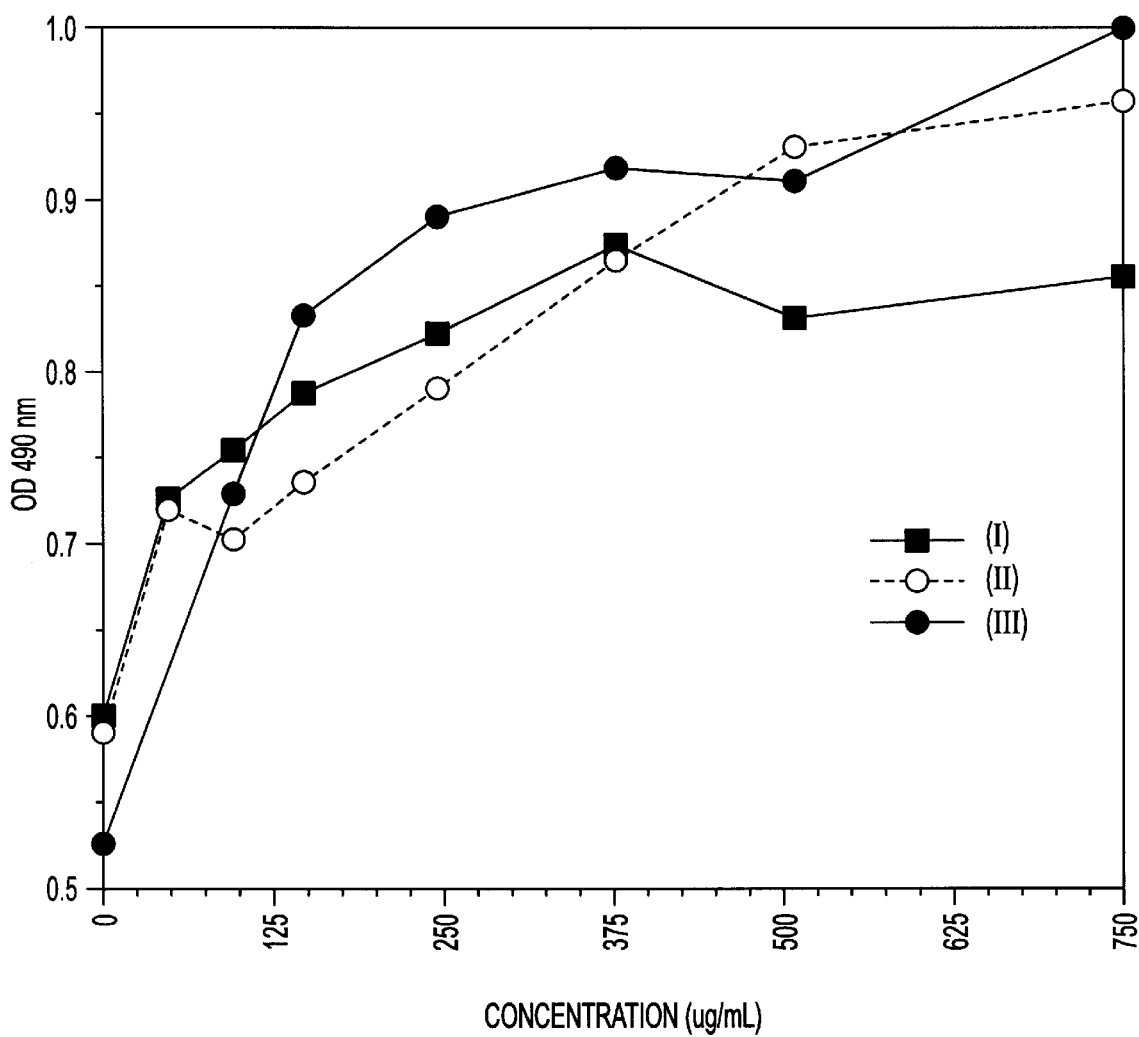
FIG. 2 is a graph showing cellular proliferation in the presence of representative compounds of Formulae (I), (II) and (III).

As illustrated in FIG. 2, when compared to untreated control, Formulae (I), (II) and (III) elicited significant dose-related fibroblast cellular accelerations at 24 hours. Each experimental set involved evaluating the activity of replicates of one compound at different concentrations using as a negative control untreated cells, and additionally in Formula (III) those treated with NVF alone. In the Formula (I) experiment, the mean OD of untreated cells was 0.601, and these increased incrementally to a mean OD of 0.878 at 375 μg/mL, an increase of 46% over control ($P<0.3^{-5}$ or $0.3\times10^{-5}$). Similarly, in the Formula (II) experiment the mean OD for untreated cells was 0.595 which peaked at 0.957 at 750 μg/mL, a 61% acceleration over control ($P<0.2^{-6}$ or $0.2\times10^{-6}$). Finally, fibroblasts in Formula (III)+NVF at 750 μg/mL accelerated 91% in 24 hours, nearly doubling their numbers compared to untreated control ($P<0.7^{-5}$ or $0.7\times10^{-5}$) (and an increase of 139% compared to NVF alone, not shown on FIG. 2).

In other experiments using Formulae (I) and (III)+NVF for 24 hours fibroblast increases were sustained in concentrations up to 1000 μg/mL; in Formula (III) a sharp decrease in fibroblasts occurred to below those of both control 0 and control NVF when concentrations reached 1500 μg/mL.

What is claimed is:

1. A wound-treating composition comprising a compound of the Formula (I),

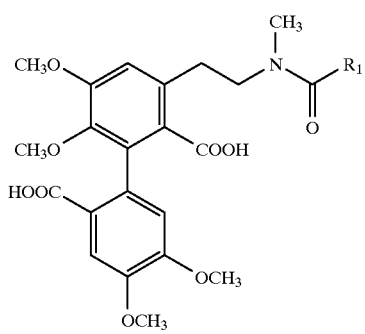

in which $R_1$ is $(CH_2)_nCH_3$ wherein n is 0 to about 10; Formula (II)

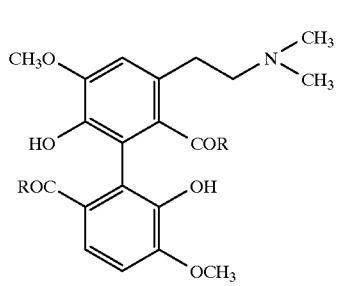

in which R is $NH(CH_2)_aCH_3$ or $O(CH_2)_aCH_3$ wherein a is 0 to about 10; or a pharmaceutically acceptable salt thereof.

2. The composition of claim 1, including a pharmaceutically-acceptable carrier.

3. The composition of claim 2, wherein said pharmaceutically-carrier is an aqueous carrier.

4. The composition of claim 3, wherein said compound is present in said aqueous carrier at a concentration of about 0.05–5 mg/mL.

5. The composition of claim 4, wherein said concentration is about 0.1–1 mg/mL.

6. The composition of claim 5, wherein said concentration is about 0.15–0.5 mg/mL.

7. The composition of claim 2, wherein said pharmaceutically-acceptable carrier comprises a member selected from the group consisting of cream, salve, foam, lotion, collagen preparation, gel and ointment.

8. The composition of claim 1 wherein n is 0 to about 5.

9. The composition of claim 1 wherein n is 0.

10. The composition of claim 1 wherein a is 0 to about 5.

11. The composition of claim 1 wherein a is 0.

12. A method of promoting mammalian cell proliferation comprising contacting mammalian cells with a cell proliferation-effective amount of a compound of claim 1, or a pharmaceutically acceptable salt thereof.

13. The method of claim 12 wherein said mammalian cells are present in a wound.

14. The method of claim 13, wherein said compound is applied to said wound so as to provide said wound with about 0.05–5.0 mg/cm² of said compound.

15. The method of claim 14, wherein about 0.1–0.5 mg/cm² of said compound is applied to said wound.

16. The method of claim 15, wherein about 0.15–0.4 mg/cm² of said compound is applied to said wound.

17. The method of claim 13, wherein said compound is applied to said wound in a pharmaceutically-acceptable liquid carrier wherein said compound is at a concentration of about 50–750 μg/mL.

18. The method of claim 13 wherein said compound is applied to said wound in a plurality of administrations of said compound.

19. A composition comprising a prepackaged wound dressing comprising a sterile bandage including a compound of claim 1, or a pharmaceutically acceptable salt thereof, which bandage is sealed within a package.

20. A composition comprising a compound of Formula (III)

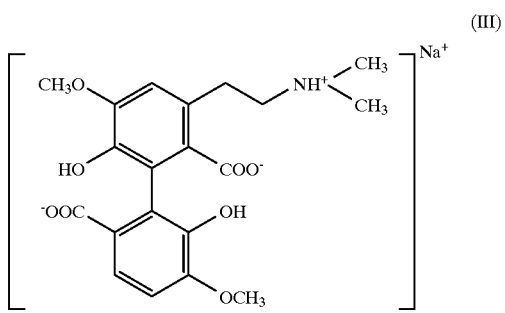

and a pharmaceutically-acceptable carrier comprising an aqueous solution of isopropanol.

21. The composition of claim 20, wherein said carrier is at a concentration of about 1–25% by volume.

22. The composition of claim 21, wherein said carrier is about 5–15% by volume.

23. A method of promoting mammalian cell proliferation in vitro comprising contacting mammalian cells in vitro with a cell proliferation-effective amount of a compound of Formula (III)

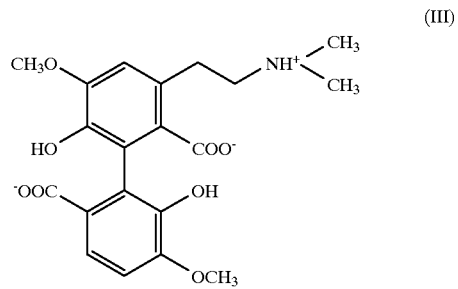

or a pharmaceutically acceptable salt thereof.

* * * * *